(12) United States Patent
Song et al.

(10) Patent No.: US 8,536,154 B2
(45) Date of Patent: Sep. 17, 2013

(54) COMPOSITION FOR ACTIVATING MITOCHONDRIA

(75) Inventors: Min Jeong Song, Yongin-si (KR); Eui Seok Shin, Yongin-si (KR); Si Young Cho, Seoul (KR); Jong Hee Sohn, Yongin-si (KR); Dae-Bang Seo, Yongin-si (KR); Wan Gi Kim, Suwon-si (KR)

(73) Assignee: Amorepacific Corporation (KR)

( * ) Notice: Subject to any disclaimer, the term of this patent is extended or adjusted under 35 U.S.C. 154(b) by 89 days.

(21) Appl. No.: 13/131,571

(22) PCT Filed: Nov. 27, 2009

(86) PCT No.: PCT/KR2009/007040
§ 371 (c)(1),
(2), (4) Date: May 26, 2011

(87) PCT Pub. No.: WO2010/062136
PCT Pub. Date: Jun. 3, 2010

(65) Prior Publication Data
US 2011/0224166 A1 Sep. 15, 2011

(30) Foreign Application Priority Data
Nov. 28, 2008 (KR) .................. 10-2008-0119311

(51) Int. Cl.
*A01N 43/04* (2006.01)
(52) U.S. Cl.
USPC ................ 514/55; 514/23; 514/54; 514/61
(58) Field of Classification Search
None
See application file for complete search history.

(56) References Cited

U.S. PATENT DOCUMENTS

| 4,826,826 A | 5/1989 | Conti |
| 2005/0004073 A1 | 1/2005 | Gislason et al. |

FOREIGN PATENT DOCUMENTS

| CN | 1861640 A | 11/2006 |
| KR | 10-2002-0073696 A | 9/2002 |
| KR | 10-2005-0091354 A | 9/2005 |
| KR | 10-2005-0043432 A | 11/2005 |
| KR | 10-2005-0104910 A | 11/2005 |

OTHER PUBLICATIONS

Kim et al. Carbohydrate Polymers (2005), vol. 62, pp. 357-368.*
Modica-Napolitano et al. Expert Reviews in Molecular Medicine (2002), vol. 4, pp. 1-19.*
Cheng et al., "Differential gene expression profiles in the hippocampus of senescence-accelerated mouse," *Neurobiology of Aging* (2007) 28: 497-506.
Nam et al., "Inhibitory effect of chitosan oligosaccharides on the growth of tumor cells," *J. Chitin Chitosan* (1999) 4 (4): 184-188.
Shon et al., "Effect of chitosan oligosaccharides on dioxin-induced CYP1A1 activity and lipid peroxidation," *J. Chitin Chitosan* (2001) 6 (3): 107-110.
Qiao et al., "Research advances of Chitosan oligosaccharides on keeping healthy," *Chinese Journal of Biochemical Pharmaceutics*, 29(3):210-213 (2008) (English Abstract).
Office Action for Chinese Patent Application No. 200980155348.5 (mailed Jul. 12, 2012).
Office Action from Chinese Patent Application No. 200980155348.5 (Apr. 3, 2013).
Yan et al. "Preparation, Characteristic and Relative Development in Its Application for Chitooligosaccharide." *Anhui Chemical Industry*, 1:24-27 (2005).

* cited by examiner

*Primary Examiner* — Patrick Lewis
(74) *Attorney, Agent, or Firm* — Merchant & Gould P.C.

(57) ABSTRACT

The present invention relates to a composition for activating mitochondria which contains a chitooligosaccharide as an active constituent. The chitooligosaccharide can increase the activity of mitochondrial enzymes and increase the amount of mitochondrial DNA, and thus it can be suitably used as an active constituent in the composition for activating mitochondria.

16 Claims, 3 Drawing Sheets

COMPOSITION FOR ACTIVATING MITOCHONDRIA

This application is a National Stage Application of PCT/KR2009/007040, filed 27 Nov. 2009, which claims benefit of Serial No. 10-2008-0119311, filed 28 Nov. 2008 in the Republic of Korea and which applications are incorporated herein by reference. To the extent appropriate, a claim of priority is made to each of the above disclosed applications.

TECHNICAL FIELD

The present disclosure relates to a composition for activating mitochondria.

BACKGROUND ART

A mitochondrion is an organelle found in most eukaryotic cells. The mitochondrion has its own DNA, i.e. mitochondrial DNA (mtDNA), independently of the nuclear DNA.

The most prominent roles of mitochondria are to produce ATP, the intracellular source of energy. ATP is produced from the electron transport chain using NADH and $FADH_2$ produced in the mitochondrial matrix via the TCA cycle. Thus produced ATP is used to activate various biosynthesis and metabolism processes demanding energy.

Also, mitochondria can transiently store calcium ions, which are important in intracellular signal transduction, in the matrix and release them to the cytoplasm when they are needed. Further, mitochondria are known to play central regulatory roles in apoptosis, cellular proliferation, cellular metabolism, and so forth.

Mitochondrial DNA is relatively susceptible to damage since it lacks its own repair mechanism unlike nuclear DNA and is free from the histone protein for protecting the DNA. It is known that the damage to the mitochondrial DNA is closely related to the onset of mitochondrial diseases. By degrading the function of mitochondria, it results in reduced synthesis of ATP, the source of energy necessary for cellular activities, and causes various diseases.

Chitosan is used in various fields, including flocculants for wastewater treatment, adsorbents for heavy metal removal, functional foods, ion exchange agents, and medical products. It is known that these functions are greatly affected by the molecular weight and deacetylation of chitosan.

Recently, it was reported that chitin, chitosan and their derivatives have decholesterolization activities of adsorbing or excreting bad cholesterols accumulated in the body, anti-cancer activities of suppressing proliferation of cancer cells, and blood pressure-lowering effects by adsorbing blood pressure-increasing chloride ions and thus reducing their absorption and excreting them out of the body. Further, it was known that they facilitate proliferation of useful intestinal bacteria and activate cells. In addition, they show various physiological activities, including blood sugar control, liver function improvement, excretion of heavy metals and pollutants, and the like. Thus, they are studied as valuable substances in the biomedicine industry.

Although chitooligosaccharides are widely used in health foods and general foods, researches about their function are insufficient. Korean Patent Publication No. 2005-0104910 discloses the function of chitooligosaccharide as an inhibitory material of the lectin-type oxidized LDL receptor 1 (LOX-1) gene in oxidized low-density lipoprotein (oxLDL), effective for prevention of arteriosclerosis. And, Korean Patent Publication No. 2005-0091354 discloses the function of chitooligosaccharide as an inhibitory material of expression of the PPAR gene which is involved in cholesterol homeostasis regulation, fat cell differentiation and fat cell synthesis as a key factor in lipid metabolism.

DISCLOSURE

Technical Problem

The present disclosure is directed to providing a composition for activating mitochondria by increasing the activity of mitochondrial enzymes and increasing the amount of mitochondrial DNA.

Technical Solution

In one general aspect, the present disclosure provides a composition for activating mitochondria which contains a chitooligosaccharide as an active constituent.

Advantageous Effects

Since the composition for activating mitochondria the present disclosure can increase the activity of mitochondrial enzymes and increase the amount of mitochondrial DNA, it can activate mitochondria and increase mitochondrial biogenesis. Accordingly, the composition according to the present disclosure can be effectively used to prevent and treat various diseases related with the decreased activity of mitochondria, such as degenerative diseases, Parkinson's disease, or the like.

MODE FOR INVENTION

Figure 1:
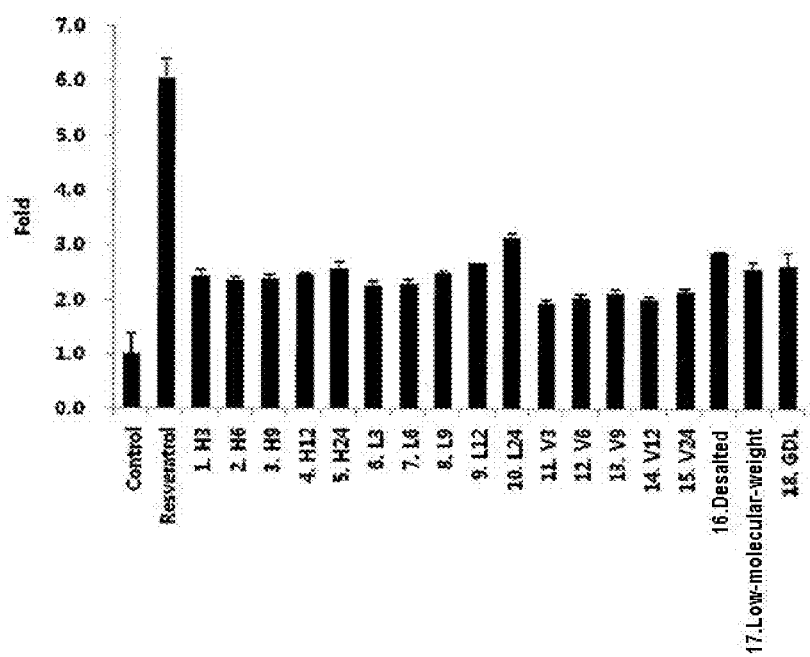
FIG. 1 shows a result of measuring the activity of the sirtuin 1 (SIRT1) protein after treating with a composition according to an embodiment of the present disclosure.

As used herein, "chitooligosaccharide" refers to a low-molecular-weight polysaccharide obtained by hydrolyzing chitosan. The "low-molecular-weight" may refer to a molecular weight smaller than 10000, more specifically 9000 or smaller. A chitooligosaccharide according to the present disclosure, which is a low-molecular-weight polysaccharide, may have a molecular weight in the range from 700 to 9000.

It is reported that chitooligosaccharides are absorbed better in the body than chitosan, and they have immune-enhancing, antioxidative (Shon Y, J. Chitin and Chitosan, 2001, 6: 107-110), and cancer cell growth suppressing (Nam MY, J. Chitin and Chitosan, 1999, 4: 184-188) activities. Further, they reported known to have the effect of inhibiting liver damage induced by carbon tetrachloride. Nevertheless, it is never known whether a composition comprising one or more selected from a group consisting of a chitooligosaccharide and a salt thereof as an active constituent has a direct effect on activation of mitochondria. The inventors of the present disclosure have measured the index indicating the facilitation of energy metabolism by chitooligosaccharides and have confirmed that one or more selected from a group consisting of a chitooligosaccharide and a salt thereof is capable of activating mitochondria.

A method for preparing the chitooligosaccharide is not particularly limited. For example, the chitooligosaccharide may be prepared by isolating and purifying chitin by crushing, desalting, deproteinating and purifying the shell of crabs, shrimps, etc., deacetylating the chitin to obtain chitosan, and then chemically or enzymatically degrading the chitosan. Specifically, it may be prepared from enzymatic degradation of chitosan.

An enzyme used for preparing the chitooligosaccharide from enzymatic degradation of chitosan is not particularly limited. For example, a cellulase may be used to enzymatically degrade the chitosan.

Specifically, when the chitosan is enzymatically degraded to prepare the chitooligosaccharide, a preparation method may be as follows. After adding purified water to chitosan and then adding 2-3% of hydrochloric acid, the mixture is stirred at 40-60° C. to prepare a chitosan dispersion having a solid content of 5-10%. Upon complete dissolution, the pH of the solution is adjusted to 4-6, and a cellulase dissolved in purified water is added as a chitosan-degrading enzyme. Then, after hydrolysis at 40-60° C. for 14-20 hours, followed by heat treatment at 80° C. for 30 minutes, deactivation of the enzyme, filtration and drying, the chitooligosaccharide can be obtained.

The one or more selected from a group consisting of a chitooligosaccharide and a salt thereof may have a molecular weight from 700 to 9000. Within this molecular weight range, the chitooligosaccharide may exhibit a superior effect of activating mitochondria. The molecular weight may vary according to the addition amount of the cellulase. When the addition amount of the cellulase is 10% based on the amount of the chitosan, a chitooligosaccharide having a molecular weight of 1000 or smaller may be obtained. When the addition amount of the cellulase is 6% based on the amount of the chitosan, a chitooligosaccharide having a molecular weight of 1500-2000 may be obtained. When the addition amount of the cellulase is 3% based on the amount of the chitosan, a chitooligosaccharide having a molecular weight of 7000-10000 may be obtained. Thus, a chitooligosaccharide having a molecular weight ranging from 700 to 9000 may be prepared by varying the addition amount of the chitosan-degrading enzyme.

The active constituent of the composition for activating mitochondria, i.e. the one or more selected from a group consisting of a chitooligosaccharide and a salt thereof, may, for example, increase the activity of sirtuin 1 (SIRT1), increase the activity of PPARγ coactivator 1α (PGC1α), or increase the copy number of mitochondrial DNA.

The active constituent may be a chitooligosaccharide or various salts thereof. The salt is not particularly limited, but it may be, for example, a chitooligosaccharide lactate (L24) having an average molecular weight of 1155. As demonstrated in the following examples, the group treated with the chitooligosaccharide lactate (L24) having an average molecular weight of 1155 among various chitooligosaccharides and their salts exhibits significant increase in the activity of SIRT1, the activity of PGC1α or the copy number of mitochondrial DNA.

SIRT1 and PGC1α may play an important role in mitochondrial biogenesis. SIRT1 is an NAD-dependent deacetylase, and is capable of increasing the production of mitochondria. PGC1α, which is a 90-kDa nuclear protein, is a transcriptional coactivator regulating genes involved in energy metabolism. PGC1α, activated by SIRT1, may increase the expression of the genes involved in ATP synthesis and mitochondrial biogenesis. In this regard, it was confirmed as described in the following examples that one or more selected from a group consisting of a chitooligosaccharide and a salt thereof can remarkably increase the activity of SIRT1 and PGC1α.

Also, the degree of mitochondrial biogenesis can be directly measured by measuring the damage of mitochondrial DNA (mtDNA) or counting the copy number of mitochondrial DNA. As demonstrated in the following examples, it was confirmed that one or more selected from a group consisting of a chitooligosaccharide and a salt thereof can remarkably increase the copy number of mitochondrial DNA.

Since the composition according to the present disclosure comprising a chitooligosaccharide as an active constituent activates mitochondria, it can be used as a composition for preventing or treating various degenerative diseases, brain diseases, neurological disorders, heart diseases, liver disease, nephropathies, pancreatic diseases or muscular diseases related with the decreased activity of mitochondria.

The degenerative disease is not particularly limited but may be, for example, degenerative arthritis, rheumatoid arthritis or osteoarthritis. These diseases may be caused by the increased expression of inflammation-related factors such as cyclooxygenase 2 (COX-2) in cartilage cells when the activity of mitochondria is decreased.

The brain disease is not particularly limited but may be, for example, dementia, Parkinson's disease, stroke, developmental delay, neuropsychiatric disorder, migraine, autism, mental retardation, seizure or palsy. These diseases may be caused by increased production and accumulation of amyloid-β, which is the main cause of brain diseases, particularly dementia, caused by reactive oxygen species produced when the activity of mitochondria is decreased.

The neurological disorder is not particularly limited but may be, for example, ptosis, optic atrophy, strabismus, retinitis pigmentosa, blindness, hearing loss, ophthalmoplegia, decreased reflex, fainting, neuropathic pain or autonomic imbalance.

The heart disease is not particularly limited but may be, for example, heart failure or cardiomyopathy. These diseases may be caused by calcium ion overload or oxidative stress that may cause problems in cardiac function when the activity of mitochondria is decreased.

The liver disease is not particularly limited but may be, for example, hypoglycemia or liver failure.

The nephropathy is not particularly limited but may be, for example, renal tubular acidosis. These diseases may be caused by increased oxidative stress due to the damage to the mitochondrial respiratory system when the activity of mitochondria is decreased.

The pancreatic disease is not particularly limited but may be, for example, exocrine pancreatic insufficiency or parathyroid insufficiency.

The muscular disease is not particularly limited but may be, for example, irritable bowel syndrome, myalgia, muscular dystrophy, gastroesophageal reflux disease, hypotension, convulsion, motor disturbance, constipation or diarrhea. These diseases may be caused by abnormal muscular motion due to reduced ATP generation when the activity of mitochondria is decreased.

The composition is not particularly limited but may be, for example, a health food composition or a pharmaceutical composition.

The health food composition may be formulated in various forms including powder, granule, tablet, capsule and drink.

If necessary, the health food composition may comprise one or more additive. The additive may include fruit juice (including concentrated fruit juice and powdered fruit juice) such as grapefruit juice, apple juice, orange juice, lemon juice, pineapple juice, banana juice, pear juice, etc.; vitamins (water-soluble and fat-soluble vitamins) such as retinol palmitate, riboflavin, pyridoxine, cyanocobalamin, sodium ascorbate, nicotinamide, calcium pantothenate, folic acid, biotin, cholecalciferol, choline bitartrate, tocopherol, β-carotene, etc.; flavors such as lemon flavor, orange flavor, strawberry flavor, grapefruit flavor, vanilla essence, etc.; amino acids, nucleic acids and salts thereof such as glutamic acid, sodium glutamate, glycine, alanine, aspartic acid, sodium aspartate, inosinic acid, etc.; plant fibers such as polydextrose, pectin, xanthan gum, glucomannan, alginic acid, etc.; and minerals such as sodium chloride, sodium acetate, magnesium sulfate, potassium chloride, magnesium chloride, magnesium carbonate, calcium chloride, dipotassium phosphate, monosodium phosphate, calcium glycerophosphate, sodium ferrous citrate, ammonium ferric citrate, ferric citrate, manganese sulfate, copper sulfate, sodium iodide, potassium sorbate, zinc, manganese, copper, iodine, cobalt, etc.

The pharmaceutical composition may further comprise a pharmaceutical adjuvant such as an antiseptic, a stabilizer, a hydrating agent, an emulsifying accelerator, a salt for control of osmotic pressure, a buffer, etc. and other therapeutically useful substance. The pharmaceutical composition may be into various formulations for oral or parenteral administration.

The formulation for oral administration may include, for example, tablet, pill, hard or soft capsule, liquid, suspension, emulsion, syrup, granule, or the like. These formulations may include, in addition to the active constituent, a diluent (e.g., lactose, dextrose, sucrose, mannitol, sorbitol, cellulose and glycine), a lubricant (e.g., silica, talc, stearic acid or its magnesium or calcium, and polyethylene glycol). The tablet may further include a binder such as magnesium aluminum silicate, starch paste, gelatin, tragacanth, methyl cellulose, sodium carboxymethyl cellulose, and polyvinylpyrrolidine. As occasion demands, it may further include a pharmaceutical additive such as a disintegrant, e.g., starch, agar, alginic acid or its sodium salt, an absorbent, a colorant, a flavor, a sweetener, or the like. The tablet may be prepared according to the commonly employed mixing, granulation or coating methods. Typical formulations for parenteral administration include isotonic aqueous solution or suspension for injection.

The dose of the active constituent may be easily determined by those skilled in the art. A daily dose of the active constituent may vary depending on various factors, including progress and stage of the disease, age and physical condition of the patient, presence or absence of complications, and so forth. In general, the composition having the aforesaid weight composition may be administered once or twice a day, in an amount of 1-500 mg/kg, specifically 30-200 mg/kg. However, the described administration dose does not limit the scope of the present disclosure by any means.

Although the content of the active constituent is not particularly limited, it may be included in an amount of 10-90 wt % based on the total weight of the composition. A tablet or a soft capsule may include the active constituent in an amount of 10-60 wt %, and a hard capsule may include the active constituent in an amount of 10-90%.

EXAMPLES

The examples and experiments will now be described. The following examples and experiments are for illustrative purposes only and not intended to limit the scope of this disclosure.

The effect of one or more selected from a group consisting of a chitooligosaccharide and a salt thereof on mitochondrial biogenesis was analyzed through in vitro experiments. In order to investigate whether one or more selected from a group consisting of a chitooligosaccharide and a salt thereof increases mitochondrial biogenesis, C2C12 muscle cells were treated with one or more selected from a group consisting of a chitooligosaccharide and a salt thereof, and then the activity of sirtuin 1 (SIRT1) and PPARγ coactivator 1α (PGC1α) promoter and the copy number of mitochondrial DNA (mtDNA) were measured.

Test Example 1

Effect on Activity of SIRT1

The activity of SIRT1 was measured using the 'SIRT1 Fluorimetric Drug Discovery Kit' (AK-555, Biomol). SIRT1 human recombinant protein and the SIRT1 substrates Fluor de Lys-SIRT1 and $NAD^+$ were supplied along with the kit. The SIRT1 protein was used in an amount of 1 U in the total reaction volume of 50 μL, and the concentration of the substrates was 50 μM and 100 μM for Fluor de Lys-SIRT1 and $NAD^+$, respectively. The chitooligosaccharide was treated at a concentration of 500 ppm. After treating with the SIRT1 protein, the substrates, and the test substance and waiting for 45 minutes, Fluor de Lys™ Developer II/2 mM nicotinamide was added and the cells were incubated at 37° C. for 30 minutes. The result was measured using the fluorescence detector Flexstation 3 (Ex. 360 nm, Em. 460 nm, Molecular Devices) on a clean-volume 96-well microplate (Corning Costar). A blank with no SIRT1 protein was used as control. 100 μM resveratrol was used as positive control, and 100 μM nicotinamide was used as negative control. As seen from Table 1, the activity of SIRT1 was measured using various chitooligosaccharides and salts thereof. The result is shown in FIG. 1. As seen from FIG. 1, most of the chitooligosaccharides resulted in increase of the SIRT1 activity (about 1.5-3 times than the control).

TABLE 1

| | Sample name | Molecular weight | Concentration |
|---|---|---|---|
| Positive control | Resveratrol | | 100 μM |
| Chitooligosaccharide hydrochloride | 1. H3 | 2654 | 500 ppm |
| | 2. H6 | 2095 | |
| | 3. H9 | 1527 | |
| | 4. H12 | 1249 | |
| | 5. H24 | 908 | |
| Chitooligosaccharide lactate | 6. L3 | 3994 | 500 ppm |
| | 7. L6 | 3310 | |
| | 8. L9 | 2257 | |
| | 9. L12 | 1719 | |
| | 10. L24 | 1155 | |
| Chitooligosaccharide ascorbate | 11. V3 | 4869 | 500 ppm |
| | 12. V6 | 4313 | |
| | 13. V9 | 3559 | |
| | 14. V12 | 3140 | |
| | 15. V24 | 2757 | |
| Desalted chitooligosaccharide | 16. Desalted | 826 | 500 ppm |
| Low-molecular-weight chitooligosaccharide | 17. Low-molecular-weight | 754 | 500 ppm |
| GDL chitooligosaccharide | 18. GDL | 1345 | 500 ppm |

In particular, chitooligosaccharide L24 having the smallest average molecular weight among the chitooligosaccharide lactates exhibited the highest SIRT1 activity, about 3.1 times that of the control. This result suggests that the chitooligosaccharide may activate mitochondria by increasing the activity of the SIRT1 protein which plays an important role in mitochondrial biogenesis.

Test Example 2

Effect on Activity of PGC1αPromoter

The activity of the PGC1α promoter was tested using transfected Huh7 cells having the PGC1α promoter. 100 μM resveratrol was used as positive control, and the cells were treated with 500 ppm of various chitooligosaccharides and salts thereof having different average molecular weights as in Test Example 1. After treating with the chitooligosaccharide for 24 hours, the cells were washed 2 times with phosphate buffered saline (PBS) and then luciferase activity was measured using the Steady Glo luciferase assay system (E2520, Promega). Specifically, 100 μL of luciferase reagent (Steady Glo Reagent) was added to a culture dish containing the cells. After incubation for 5 minutes, the cells were transferred to a 96-well plate and fluorescence was measured using a fluorescence detector (luminometer).

TABLE 2

| Sample name | | Molecular weight | Concentration |
|---|---|---|---|
| Positive control | Resveratrol | | 100 μM |
| Chitooligosaccharide hydrochloride | 1. H3 | 2654 | 500 ppm |
| | 2. H6 | 2095 | |
| | 3. H9 | 1527 | |
| | 4. H12 | 1249 | |
| | 5. H24 | 908 | |
| Chitooligosaccharide lactate | 6. L3 | 3994 | 500 ppm |
| | 7. L6 | 3310 | |
| | 8. L9 | 2257 | |
| | 9. L12 | 1719 | |
| | 10. L24 | 1155 | |
| Chitooligosaccharide ascorbate | 11. V3 | 4869 | 500 ppm |
| | 12. V6 | 4313 | |
| | 13. V9 | 3559 | |
| | 14. V12 | 3140 | |
| | 15. V24 | 2757 | |
| GDL chitooligosaccharide | 16. GDL | 1345 | 500 ppm |
| Desalted chitooligosaccharide | 17. Desalted | 826 | 500 ppm |
| Low-molecular-weight chitooligosaccharide | 18. Low-molecular-weight | 754 | 500 ppm |

Figure 2:
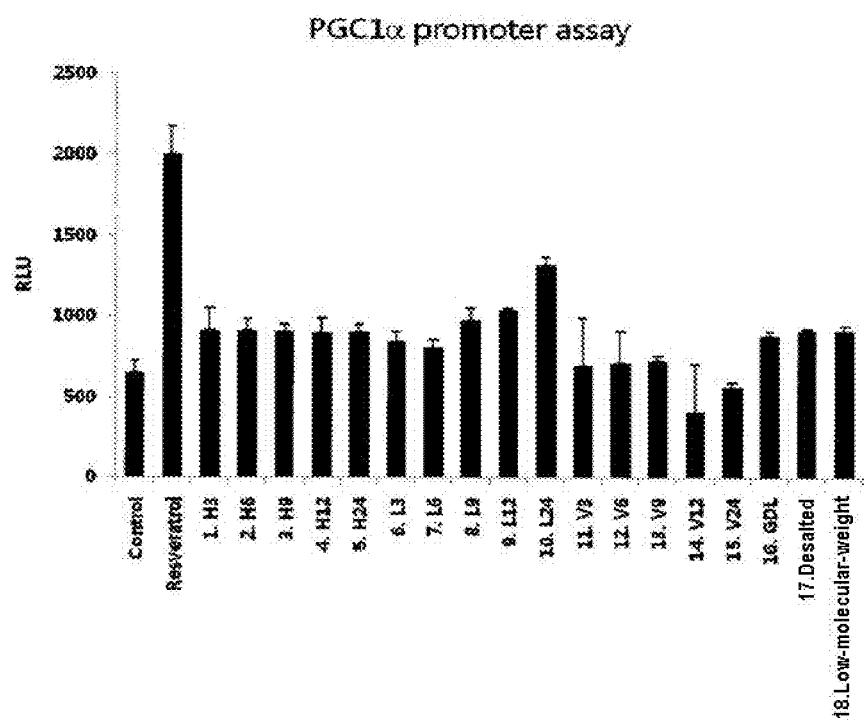
FIG. 2 shows a result of measuring the activity of the PPARγ coactivator 1α (PGC1α) promoter after treating with a composition according to an embodiment of the present disclosure.

As seen from FIG. 2, most of the chitooligosaccharides excluding the chitooligosaccharide ascorbate increased the activity of the PGC1α promoter by about 1.2-2 times. In particular, chitooligosaccharide L24 having an average molecular weight of 1155 exhibited the highest PGC1α promoter activity as in the SIRT1 activity assay of Test Example 1. The fact that the activity of the PGC1α promoter is increased by the chitooligosaccharide suggests that the chitooligosaccharide may increase mitochondrial biogenesis and activate mitochondria.

Test Example 3

Effect on Copy Number of Mitochondria (1) Culturing and Differentiation of C2C12 Cells Mouse-derived C2C12 cells were acquired from the ATCC. The C2C12 cells were cultured in 4.5 g/L glucose Dulbecco's modified Eagle's medium (DMEM) containing 10% fetal bovine serum and 1% penicillin/streptomycin. When the cell concentration in the culture dish reached 95-100%, the culture medium was replaced with 4.5 g/L glucose DMEM containing 2% horse serum and 1% penicillin/streptomycin so that the cells could differentiate into muscle cells and then cultured for about 5 days.

(2) Effect on Copy Number of Mitochondria

The C2C12 cells that had differentiated into muscle cells were treated for 24 hours with 50 μM resveratrol as positive control or with 500 ppm of the chitooligosaccharide lactate having an average molecular weight of 1155, which showed the best effect in Test Examples 1 and 2, as described in Table 3. After washing once with PBS, total DNA was separated using a DNA isolation kit (DNeasy Blood & Tissue Kit, 69504, Qiagen).

TABLE 3

| | Sample name | Molecular weight | Concentration |
|---|---|---|---|
| Positive control | Resveratrol | | 50 μM |
| Chitooligosaccharide lactate | L24 | 1155 | 500 ppm |

Subsequently, quantitative PCR was carried out as follows in order to determine the copy number of mitochondrial DNA. Primers Mtco1-F (5'-TATCCAACTCATCCCTTGA-CATCG-3', SEQ ID NO: 1) and Mtco1-R (5'-GAG-TAGCGTCGTGGTATTCCTG-3', SEQ ID NO: 2) for amplifying a portion (250-bp size) of the Mtco1 gene were synthesized based on the known mitochondrial DNA base sequence of mouse (Xiao-Rui Cheng, *Neurobiol. Aging*, 2007, 28: 297-506). The copy number of mitochondrial DNA is determined by dividing the number of mitochondrial genes by the genes expressed in the nucleus. β-actin (TaqMan Gene Expression Assays, Applied Biosystems, NM_007393.3) was selected as the nuclear gene. PCR condition for the Mtco1 gene was as follows. 20 μL of reaction solution containing 10 μL of iQ™ SYBR Green Supermix (170-8880, BioRad) and 5 pmole of each primer was treated at 95° C. for 3 minutes, followed by 50 cycles of 30 seconds at 95° C., 30 seconds at 55° C. and 20 seconds at 72° C. Increase in fluorescence with the amplification of genes was measured in real time using the Rotor-Gene apparatus (RG3000, Corbett Research). PCR condition for the β-actin was as follows. 20 μL of reaction solution containing 10 μL of QuantiTect™ Probe PCR Kit (Qiagen, 204343) and 1 μL of each primer was treated at 50° C. for 2 minutes and then at 95° C. 10 minutes, followed by 50 cycles of 15 seconds at 95° C. and 1 minute at 60° C. Increase in fluorescence with the amplification of genes was measured in real time.

Figure 3:
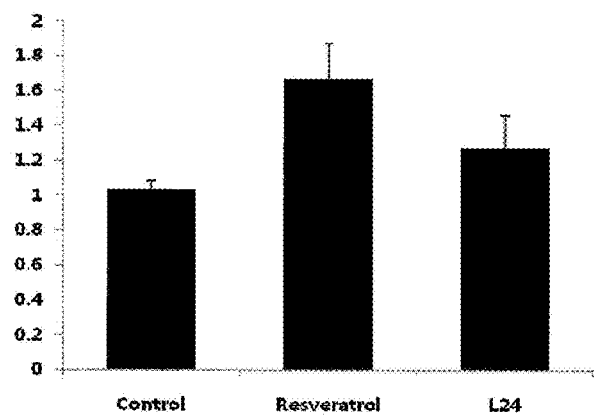
FIG. 3 shows a result of counting the copy number of mitochondrial DNA after treating with a chitooligosaccharide lactate having an average molecular weight of 1155 according to an embodiment of the present disclosure.

The result is shown in FIG. 3. As seen from FIG. 3, the group treated with 500 ppm of the chitooligosaccharide lactate having an average molecular weight 1155 exhibited about 30% increased copy number of mitochondrial DNA as compared to the control group. The increase in the mitochondrial DNA copy number is a direct indicator of increased mitochondrial biogenesis. Thus, as also seen from the increased SIRT1 and PGC1α promoter activity, it was confirmed that the chitooligosaccharide activates mitochondria and increases mitochondrial biogenesis.

The formulation examples of the composition will now be described. The following examples are for illustrative purposes only and not intended to limit the scope of this disclosure.

Formulation Example 1

Preparation of Soft Capsule

Chitooligosaccharide (80 mg), vitamin E (9 mg), vitamin C (9 mg), palm oil (2 mg), hydrogenated vegetable oil (8 mg), beeswax (4 mg) and lecithin (9 mg) were mixed according to a commonly employed method to prepare a soft capsule filling solution. 400 mg of the filling solution was filled per capsule. Separately from this, a soft capsule sheet was prepared using 66 parts by weight of gelatin, 24 parts by weight of glycerin and 10 parts by weight of sorbitol, which was filled with the filling solution to prepare a soft capsule containing 400 mg of the composition according to the present disclosure.

Formulation Example 2

Preparation of Tablet

Chitooligosaccharide (80 mg), vitamin E (9 mg), vitamin C (9 mg), galactooligosaccharide (200 mg), lactose (60 mg) and maltose (140 mg) were mixed, granulated using a fluidized-bed dryer, and then sugar ester (6 mg) was added. The resulting composition (504 mg) was prepared into a tablet according to a commonly employed method.

Formulation Example 3

Preparation of Drink

Chitooligosaccharide (80 mg), vitamin E (9 mg), vitamin C (9 mg), glucose (10 g), citric acid (0.6 g) and liquid oligosaccharide (25 g) were mixed. After adding 300 mL of purified water, the mixture was filled in a bottle, with 200 mL each. Then, after sterilizing at 130° C. for 4-5 seconds, a drink was prepared.

Formulation Example 4

Preparation of Granule

Chitooligosaccharide (80 mg), vitamin E (9 mg), vitamin C (9 mg), anhydrous crystalline glucose (250 mg) and starch 550 mg were mixed, granulated using a fluidized-bed granulator, and then filled in a pouch.

While the present disclosure has been described with respect to the specific embodiments, it will be apparent to those skilled in the art that various changes and modifications may be made without departing from the spirit and scope of the disclosure as defined in the following claims.

What is claimed is:

1. A method for activating mitochondria in a subject, comprising administering an effective amount of a chitooligosaccharide lactate to the subject.

2. The method for activating mitochondria according to claim 1, wherein the chitooligosaccharide lactate has a molecular weight from 700 to 9000.

3. The method for activating mitochondria according to claim 1, wherein the chitooligosaccharide lactate increases the activity of sirtuin 1 (SIRT1).

4. The method for activating mitochondria according to claim 1, wherein the chitooligosaccharide lactate increases the activity of PPARγ coactivator 1α (PGC1α).

5. The method for activating mitochondria according to claim 1, wherein the chitooligosaccharide lactate increases the copy number of mitochondrial DNA.

6. The method for activating mitochondria according to claim 1, wherein the method is a method for preventing or treating degenerative diseases, brain diseases, neurological disorders, heart diseases, liver diseases, nephropathies, pancreatic diseases or muscular diseases.

7. The method for activating mitochondria according to claim 1, wherein the method is a method for preventing or treating degenerative arthritis, rheumatoid arthritis or osteoarthritis.

8. The method for activating mitochondria according to claim 1, wherein the method is a method for preventing or treating dementia, Parkinson's disease, stroke, developmental delay, neuropsychiatric disorder, migraine, autism, mental retardation, seizure or Palsy.

9. The method for activating mitochondria according to claim 1, wherein the method is a method for preventing or treating ptosis, optic atrophy, strabismus, retinitis pigmentosa, blindness, hearing loss, ophthalmoplegia, decreased reflex, fainting, neuropathic pain or autonomic imbalance.

10. The method for activating mitochondria according to claim 1, wherein the method is a method for preventing or treating heart failure or cardiomyopathy.

11. The method for activating mitochondria according to claim 1, wherein the method is a method for preventing or treating hypoglycemia or liver failure.

SEQUENCE LISTING

```
<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: primer

<400> SEQUENCE: 1
tatccaactc atcccttgac atcg                                            24

<210> SEQ ID NO 2
<211> LENGTH: 22
<212> TYPE: DNA
<213> ORGANISM: Artificial Sequence
<220> FEATURE:
<223> OTHER INFORMATION: primer

<400> SEQUENCE: 2
gagtagcgtc gtggtattcc tg                                              22
```

12. The method for activating mitochondria according to claim 1, wherein the method is a method for preventing or treating renal tubular acidosis.

13. The method for activating mitochondria according to claim 1, wherein the method is a method for preventing or treating exocrine pancreatic insufficiency or parathyroid insufficiency.

14. The method for activating mitochondria according to claim 1, wherein the method is a method for preventing or treating irritable bowel syndrome, myalgia, muscular dystrophy, gastroesophageal reflux disease, hypotension, convulsion, motor disturbance, constipation or diarrhea.

15. The method for activating mitochondria according to claim 1, wherein the chitooligosaccharide lactate is administered in the form of a composition, the composition being a health food composition or a pharmaceutical composition.

16. The method for activating mitochondria according to claim 1, wherein the chitooligosaccharide lactate is administered in the form of a composition, and wherein the composition comprises 10-90 wt % of chitooligosaccharide lactate based on the total weight of the composition.

* * * * *